(12) United States Patent
Delaperriere et al.

(10) Patent No.: US 7,420,160 B2
(45) Date of Patent: Sep. 2, 2008

(54) PHANTOM FOR MEASURING IONIZING RADIATION

(75) Inventors: Marc Delaperriere, Erlangen (DE); Tim Use, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 164 days.

(21) Appl. No.: 11/477,343

(22) Filed: Jun. 28, 2006

(65) Prior Publication Data

US 2007/0014928 A1 Jan. 18, 2007

(30) Foreign Application Priority Data

Jun. 30, 2005 (DE) .................. 10 2005 030 648

(51) Int. Cl.
*G01D 18/00* (2006.01)
(52) U.S. Cl. .................................. 250/252.1
(58) Field of Classification Search ............... 250/252.1
See application file for complete search history.

(56) References Cited

U.S. PATENT DOCUMENTS

| | | | |
|---|---|---|---|
| 3,864,568 A * | 2/1975 | Helgesson | 250/252.1 |
| 5,006,714 A | 4/1991 | Attix | |
| 5,261,279 A | 11/1993 | Wolf et al. | |
| 5,621,214 A | 4/1997 | Sofield | |
| 5,635,709 A | 6/1997 | Sliski et al. | |
| 6,207,952 B1 | 3/2001 | Kan et al. | |
| 7,193,220 B1 * | 3/2007 | Navarro | 250/374 |

FOREIGN PATENT DOCUMENTS

| DE | 41 41 324 A1 | 6/1992 |
|---|---|---|
| DE | 41 06 932 A | 9/1992 |
| DE | 41 06 932 A1 | 9/1992 |
| JP | 2004-129678 A | 4/2004 |

OTHER PUBLICATIONS

Blue Phantom: The advanced 3D beam analyzing system (Scanditronix Wellhöfer) undated [online] [retrieved on Jan. 29, 2008] Retrieved from <URL: http://www.stratecservices.nl/images/products/Blue_Phantom.pdf>.*
Institut für Mikro- und Informationstechnik der Hahn-Schickard-Gesellschaft (HSG.IMIT), "Neigungssensor erhält Innovationspreis," 1 Seite, http://www.innovationsreport.de/html/berichte/veranstaltungen/special-1692.html, vom Nov. 4, 2002.
German Office Action, not a publication.
Scanditronix-Wellhöfer, "Blue Phantom-The advanced 3D beam analyzing system, Competence in radiotherapy dosimetry," www.scanditronix-wellhofer.com, 12 pages; Sep. 20, 2005.
Institut für Mikro- und Informationstechnik der Hahn-Schickard-Gesellschaft (HSG.IMIT), "Neigungssensor erhält Innovationspreis," 1 Page, http://www.innovationsreport.de/html/berichte/veranstaltungen/special-1692.html, Apr. 11, 2002.
German Office Action dated Apr. 10, 2006.

* cited by examiner

*Primary Examiner*—Constantine Hannaher
(74) *Attorney, Agent, or Firm*—Brinks, Hofer, Gilson & Lione (57) ABSTRACT

A water phantom is described, having a detector that is positionable in a container filled with water for measuring an ionizing radiation. The water phantom has at least one sensor for ascertaining an orientation of a positioning device, relative to a water surface. The orientation determination is based either on distances relative to the water surface that are measured by spacing sensors or, on inclinations, each measured by a gravity-sensitive inclination sensor.

32 Claims, 4 Drawing Sheets

PHANTOM FOR MEASURING IONIZING RADIATION

RELATED APPLICATIONS

This application claims the benefit of priority to German patent application DE 10 2005 030 648.9, filed on Jun. 30, 2005.

TECHNICAL FIELD

This application relates to a water phantom for measuring ionizing radiation, such as X-radiation or gamma radiation used for radiation therapy, or high-energy electron, proton and ion radiation.

BACKGROUND

The human body is predominantly comprised of water. The water phantom is especially well suited for determining the effect of the radiation on the human body. A water phantom may measure the radiation penetrating a container filled with water. The radiation may be measured by a detector or an array of individual detectors that can be positioned inside the water in various measurement positions by a positioning device.

The local ionization of the water caused by radiation can be measured, and a conclusion can be drawn about the applicable local energy input of the radiation to the water. By positioning the detector in various measurement positions along the radiation direction, a radiation profile of the penetration depth may be determined. By positioning the detector in various measurement positions on a straight line perpendicular to the radiation direction, the radiation profile transverse to the propagation direction may be determined. The radiation profiles and other parameters that characterize the radiation may hereinafter be referred to by the general term radiation "parameters".

The radiation parameters are ascertained at regular time intervals, typically once a day. The radiation parameters are compared with set-point values in order to assure constant quality of the radiation dose and, if needed, to recalibrate the radiation source. Often, comprehensive regular monitoring of the radiation parameters is prescribed by law. Monitoring operations can take from half a day to several days to complete.

Depending on the radiation source used, the radiation strikes the water phantom in either a horizontal or vertically downward-oriented direction. Water phantoms usually have a container, open at the top, for the water. In the case of a vertically downward-oriented radiation direction, the radiation penetrates the water directly from above. In that case, the penetration depth of the radiation into the water is determined by the spacing of the detector from the water surface. This spacing must therefore be known as accurately as possible to avoid errors in measurement of the radiation parameters, and especially of the radiation profile as a function of the penetration depth. For a horizontal radiation direction, the radiation first penetrates the outer wall of the container before penetrating the water in the container. The influence of the outer wall on the radiation is taken into account in ascertaining the radiation parameters. If the water level is too low, there is a possibility that, with radiation extending close to the water surface, scattering of the radiation will occur at the water surface. Scattering may cause the radiation parameters to be incorrectly ascertained. The positioning device must also be oriented relative to the radiation direction, so that the radiation parameters can be spatially associated as accurately as possible with the radiation.

Prior to measuring the radiation, the positioning device is oriented with respect to the water surface, to make it possible to use spacing, or distance, of the detector from the water surface into account in ascertaining the radiation parameters. Typically, the container of the water phantom is block-shaped, and, with the aid of the positioning device, the detector can be moved to the various measurement positions. The motion is substantially horizontal in two directions of motion perpendicular to one another along the lower edges of the container, and substantially vertically in a further direction of motion along the sides of the container. When the positioning device is oriented such that the two essentially horizontal directions of motion are exactly horizontal and thus parallel to the water surface or, alternatively, the vertical direction of motion is exactly plumb and hence perpendicular to the water surface, then, by determining the distance of the detector from the water surface at an arbitrary measurement position, the distance of the detector from the water surface at any other measurement position is also ascertainable. With a horizontal radiation direction, the radiation extends parallel to the water surface, while with a vertical radiation direction the radiation extends perpendicular to the water surface. Because of the orientation of the positioning device with respect to the water surface, the positioning device is also oriented relative to the radiation direction.

Frequently, the positioning device is solidly connected to the container, and the three directions of motion extend precisely parallel to the edges of the container. The container, together with the positioning device, is tiltably supported about two horizontal axes. The positioning device can be oriented relative to the water surface, using at least two measuring scales located vertically on the sidewalls, for ascertaining the water level. When the water level is being read off from one of the measuring scales, an error in measurement can easily occur, for instance from parallax that is dependent on the viewing angle or from a meniscus that the water forms with respect to the side walls of the container. The container is supported on feet that can be adjusted in height by means of a screw thread. Water phantoms are also known whose orientation is adjustable by the user, such as with electric motors.

In a water phantom product known as "Blue Phantom," made by Scanditronix Wellhöfer GmbH (Schwarzenbruck, Germany), the water level may be measured by a spacing sensor, located above the water surface in a corner of the container. The spacing sensor uses an echo pulse principle. For the "Blue Phantom" water phantom, a water reservoir communicates with the container via a supply line, and a water pump is regulated as a function of the water level ascertained by the spacing sensor, such that the water maintains an intended level despite any possible evaporation of the water. Adjusting screws provide for manual orientation of the positioning device relative to the container.

The orientation of a positioning device with respect to the water surface is complex. There is the risk that the orientation will be done imprecisely, causing the radiation parameters to be ascertained incorrectly. Ascertaining and adjusting the orientation of the positioning device by the user is time-consuming. The time required for this adjustment reduces the time available for the diagnostic or therapeutic use of the particular radiation source.

SUMMARY

A water phantom has a detector positionable in various measurement positions for measuring ionizing radiation in a container filled with water. The water phantom has a sensor for ascertaining an orientation of a positioning device to facilitate positioning the detector relative to the water surface. This positioning is based either directly on distances with respect to the water surface that are measured by spacing sensors, or on inclination angles, each measured with at least one inclination sensor, relative to a local gravity vector.

At least two spacing sensors for ascertaining distances from respective proximate points on the water surface, or at least one inclination sensor for ascertaining an inclination angle with respect to the local gravity vector permits the orientation of the positioning device relative to the water surface to be ascertained. Since the surface of the water orients itself in accordance with gravity, each of the measurement techniques provides precise water surface measurements.

Based on the distances from the water surface measured by the at least two spacing sensors of the water phantom, the orientation of the positioning device for the detector with respect to the water surface may be determined.

For example, with two spacing sensors, each measuring a spacing perpendicular to the water surface, it is possible to ascertain the orientation as an inclination angle about a horizontal axis of inclination, perpendicular to a connecting line between the two spacing sensors. Based on the at least one inclination angle, which is ascertainable relative to the local gravity vector by an inclination sensor, it is possible to ascertain the orientation of the positioning device with respect to the water surface.

Ascertaining the orientation, in particular in the form of an inclination angle, for instance with the sensors as part of an electrical measuring device, permits fast adjustment of the orientation. The two spacing sensors and one inclination sensor each represent a measuring device for ascertaining an inclination angle.

With three spacing sensors that together define a triangle, the orientation of the positioning device is ascertained as inclination angles about two different axes of inclination. The inclination of the positioning device is characterized with respect to the water surface. The three spacing sensors may be disposed such that they form a right triangle. With the two spacing sensors on the ends of the one side of the triangle, the inclination about a horizontal axis of inclination perpendicular to the one side of the triangle can be ascertained. With the spacing sensors on the ends of the other side of the triangle, the inclination about a horizontal axis of inclination perpendicular to the other side of the triangle may be ascertained.

Two or more spacing sensors may mechanically determine the distance to the water surface. These spacing sensors may, for example, each include a hollow body floating on the water surface and having a rod guided vertically close to an optical sensor. The optical sensor may be located near the level of the positioning device and, from a scale on the rod, ascertain the floating height of the hollow body.

Alternatively, the spacing sensors may ascertain the distance to the water surface based on the transit time of ultrasound waves reflected from a proximate point on the water surface. Contactless measurement of the applicable distance is possible. The spacing sensors may have an ultrasound emitter, oriented in a direction perpendicular to the surface of the water and an ultrasound receiver that receives the ultrasound reflected vertically. As the speed of sound in water or air is known, the distance between the sensor and the water surface can be determined from the transit time between the emission and the reception of the ultrasound waves.

In a further aspect, the spacing sensors may be based on light, such as laser light, reflected from the water surface. As a result, contactless measurement of the spacing is possible.

Suitable spacing sensors using the principle of laser-based interferometry or laser-based triangulation are widely known.

With the aid of two inclination sensors, located at an angle to one another, it is possible to ascertain the orientation of the positioning device. The orientation is provided by inclination about two different horizontal axes of inclination, characterizing the inclination of the positioning device relative to the water surface. The two inclination sensors may be located such that the two axes of inclination are oriented perpendicular to one another, such that one of the two inclination sensors determines an inclination angle about a first horizontal axis of inclination, and another inclination sensor determines the inclination about a second horizontal axis of inclination. Instead of two inclination sensors, each with one axis of inclination, it is also possible to use one inclination sensor that has two sensitive axes of inclination.

DETAILED DESCRIPTION

Exemplary embodiments may be better understood with reference to the drawings, but these examples are not intended to be of a limiting nature. Like numbered elements in the same or different drawings perform equivalent functions. When a specific feature, structure, or characteristic is described in connection with an example, it will be understood that one skilled in the art may effect such feature, structure, or characteristic in connection with other examples, whether or not explicitly stated herein.

Figure 1:
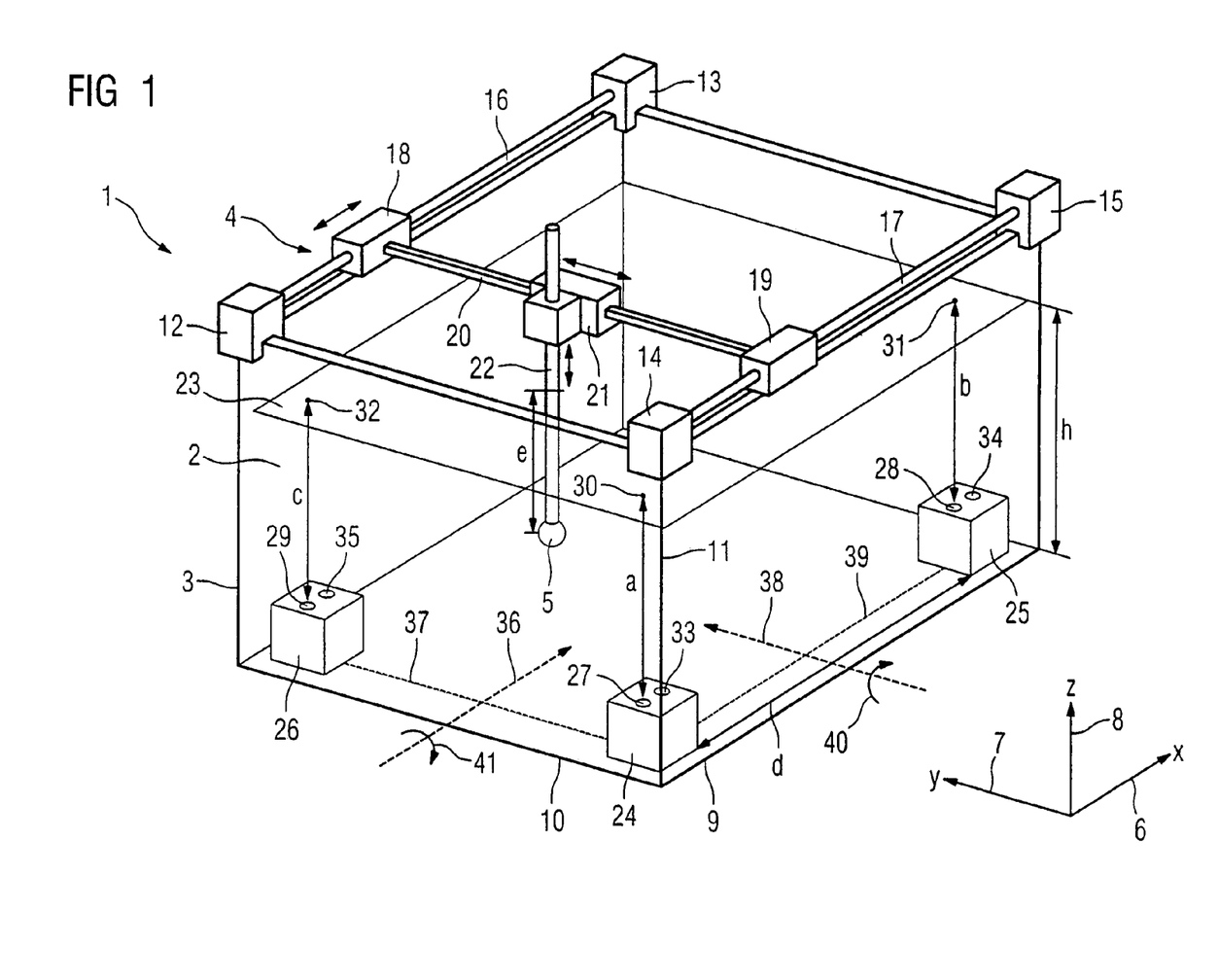
FIG. 1 shows a perspective view of a water phantom with a positioning device for a detector secured to its water-filled container.

FIG. 1 is a perspective view of a water phantom 1 having a block shaped container 3 suitable for filling with water 2, and having an open top. A positioning device 4 is secured to the block-shaped container 3. By using the positioning device 4, a detector 5 for measuring ionizing radiation penetrating the water 2 can be positioned inside the water 2 in various measurement positions in three dimensions.

A Cartesian coordinate system having x, y and z axes is used. The coordinate axes 6-8 extend parallel to the edges 9-11 of the container 3. Other coordinate systems with or without axes parallel to the container 3 may be used.

The positioning device 4 is secured to the upper corners of the container 3 with fastening elements 12-15. A first rail 16 and a second rail 17 are held on opposing sides of the container 3 by a pair of the fastening elements 12, 13 and 14, 15, respectively. A first retaining element 18 and a second retaining element 19, respectively, are displaceable parallel to one another along the rails in the direction of the x-axis 6. The two retaining elements 18, 19 are joined by a third rail 20, extending horizontally above or in the water, on which a third retaining element 21 is displaceable in the direction of the y-axis 7. A rod 22, which is displaceable in the direction of the z-axis 8, is held by the third retaining element 21. The detector 5 is secured to an end of the rod 22 that protrudes into the water 2 and with which the local radiation dose can be measured. To measure radiation penetrating vertically from above into the water 2, the detector 5 may be located at some distance laterally from the rod 22, for instance by means of a connection extender (not shown), so that the rod 22 and the third retaining element 21 may not absorb significant radiation before it reaches the detector 5.

The orientation of the positioning device 4 with respect to the water surface 23 may, for example, be measured using three spacing sensors 24-26, which are disposed to form a right triangle. Based on the known disposition of the spacing sensors 24-26 on the container 3, on which the positioning device 4, with the four fastening elements 12-15, is disposed in a predetermined relative position, it is possible to determine the orientation of the positioning device 4 relative to the water surface 23 without impairing the freedom of motion of the detector 5. The three spacing sensors 24-26 may be located in three of the four lower corners of the container 3, below the water surface 23. It is equally possible to dispose the spacing sensors 24-26 above the water surface 23, for example, close to the fastening elements 12-15.

The spacing sensors 24, 25 and 26 may ascertain a respective distance a, b and c from the water surface 23 based on a respective transit time of ultrasound waves reflected from the water surface 23. The ultrasound waves are emitted by a respective ultrasound emitter 27, 28 and 29 of the spacing sensors 24, 25 and 26 respectively, in a direction vertically upward toward the water surface 23, and strike the water surface at points 30, 31 and 32, respectively. The ultrasound waves are at least partly reflected vertically downward from the water surface 23 and are received by a respective ultrasound receivers 33, 34 and 35 of the spacing sensors 24, 25 and 26. From the respective transit times between the emission and the receiving of the ultrasound waves, taking the known propagation speed of ultrasound waves in the water 2 into account, the respective spacings a, b and c from the water surface 23 can be ascertained.

Based on two distances, for example, a and c, which are measured by the spacing sensors 24 and 26, respectively, located on the side wall of the container 3 parallel to the y axis 7, an inclination of the positioning device 4 about a horizontal axis of inclination 36 perpendicular to a connecting line 37 between the respective two spacing sensors 24 and 26, can be ascertained. This axis of inclination 36 is parallel to the x-axis 6. Further, based on the two distances a and b, which are measured by the respective spacing sensors 24 and 25 that are located on the side wall of the container 3 parallel to the x axis 6, an inclination of the positioning device 4 about a horizontal axis of inclination 38 perpendicular to a connecting line 39 between the respective two spacing sensors 24 and 25 can be ascertained. This axis of inclination 38 is parallel to the y-axis 7. An inclination about the axis of inclination 38 is ascertained based on the distances a and b that are measured by the spacing sensors 24 and 25, respectively, on the sidewall of the container 3 that is parallel to the x-axis 6. If the spacing sensor 25 measures the spacing b and the spacing sensor 24 measures the spacing a, the angle of inclination $\alpha$ of the positioning device 4 about the axis of inclination 38 that is parallel to the y axis 7 may be computed from $\tan\alpha = (b-a)/d$, where d is the spacing between the two spacing sensors 24 and 25.

In another embodiment, it is possible to use light-based, in particular laser light-based spacing sensors, by which the respective distances a-c can be ascertained based on light. For example, when laser light is used, the light may be reflected from the water surface 23, and ascertaining the various distances a-c may be done using the principle of interferometry. The inclination of the positioning device 4 may be obtained just once before measuring the radiation in many uses, but multiple measurements may be performed in other uses.

In yet another embodiment, an inclination angle about one, two or more axes of inclination 36 and 38 can be ascertained, as well as the vertical position of the positioning device 4 relative to the water surface 23. Taking into account an extension length of the rod 22, it is possible to determine the applicable immersion depth e of the sensor 5 with respect to the water surface 23. The extension length can be determined, for example, by means of a potentiometer that is integrated with the third retaining element 21, or by means of an optical sensor integrated with the third retaining element 21 for detecting markings that mark various extension lengths on the rod 22.

The vertical position of the sensor 5 can be determined based on one of the three distances a, b or c, or based on a mean value $m=(a+b+c)/3$ of the three distances a-c or another calculation. Together with the inclination about the two axes of inclination 36, 38, it is possible to determine the immersion depth e of the detector 5 as a function of the x and y coordinates. By ascertaining the vertical position during the measurement of the radiation, the current water level h can be determined. During the course of the measurement, this level may decrease because of evaporation or increase due to thermal expansion.

The immersion depth e of the detector 5 relative to the water surface 23 is important for a radiation direction that is oriented vertically downward. If an incorrect immersion depth e from the water surface 23 is determined, the result can be an unwanted offset in the radiation profile at the penetration depth. In a treatment of a patient with the radiation source following the measurement of the radiation, this can lead to an incorrect setting of the radiation source.

With the aid of the positioning device 4, the detector 5 may be displaceable by a motor to a particular measurement position. During the course of the measurement of radiation, the detector 5 may be positioned successively at various measurement positions, so that at the particular measurement position, a measurement of the local dose is made with the detector 5. Measurement errors resulting in position inaccuracy of the detector 5 relative to the water surface 23 may be avoided by means of a control unit (not shown) for automatic positioning of the detector 5 as a function of the orientation of the positioning device 4 of the detector 5 relative to the water surface 23.

In an example, the orientation of the positioning device 4 has an angle of inclination $\alpha$ in the inclination direction 40 shown about the axis of inclination 38 that is parallel to the y-axis 7. The origin of the coordinate system is assumed to be located at the bottom of the container 3 at the intersection of the two axes of inclination 36 and 38. The aforementioned orientation, upon an originally intended positioning from a position at the origin of the coordinate system to the measurement position having the coordinates x, y and z, can be taken into account. A position is adapted to the applicable inclination, such as the measurement position having the coordinates $x'=\cos(\alpha)x-\sin(\alpha)z$, $y'=y$ and $z'=\cos(\alpha)z+\sin(\alpha)x$. Taking an inclination with the angle of inclination p into account in the direction of inclination 41 shown about the axis of inclination 36 that is parallel to the x-axis 6 is done in an analogous way.

In addition to accounting for the inclination, the control unit may take the vertical position of the positioning device 4 relative to the water surface 23 into account in performing automatic positioning.

Measurement errors from a positioning inaccuracy of the detector 5 relative to the water surface 23 may be avoided by means of an evaluation unit (not shown) for evaluating the measured radiation as a function of the orientation of the positioning device 4. As a result, the measurement of the radiation can be done in an undistorted way. For instance, for a 3D grid of intended measurement positions, the location, varied because of the applicable orientation, of the actual measurement positions from the intended measurement positions should be taken into account.

Besides simply accounting for the orientation, in the form of an inclination, an embodiment of the evaluation unit additionally takes into account the vertical position of the positioning device 4 relative to the water surface 23.

Figure 2:
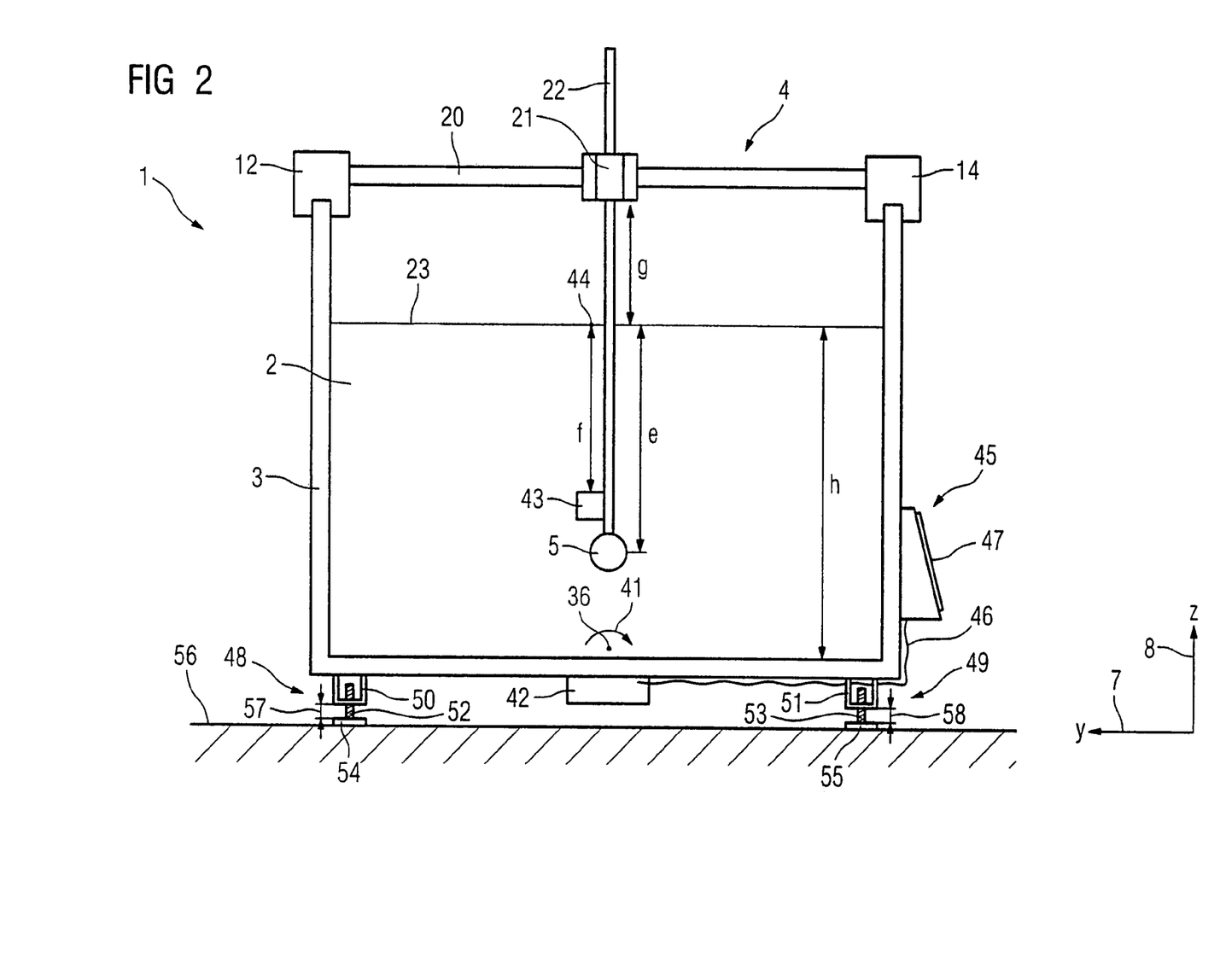
FIG. 2 shows a side view of the water phantom of FIG. 1, in which the orientation of the positioning device is ascertainable with the aid of an inclination sensor and is adjustable with the aid of adjustable-height feet.

FIG. 2 shows a side view of the water phantom 1 of FIG. 1. The orientation of the container 3, and thus also of the positioning device 4 that is solidly joined to the container 3 relative to the water surface 23 is ascertainable by two inclination sensors located on the container 3. In this side view, only the inclination sensor 42 is shown. The inclination sensor 42 measures the inclination of the positioning device 4 about the axis of inclination 36 oriented parallel to the x-axis 6 can be ascertained. There is also a second inclination sensor on the container 3 which ascertains the inclination of the positioning device 4 about the other axis of inclination 38. Retaining elements 18 and 19 are concealed behind the fastening elements 12 and 14.

One embodiment of the inclination sensor 42 has electrodes that are immersed at least partially into an electrically conductive liquid for ascertaining an inclination angle based on an electrical resistance between the electrodes that is dependent on the inclination of the liquid. Alternatively, the inclination sensor 42 may have a capacitor, filled at least partly with an electrically conductive liquid or dielectric liquid, for ascertaining the inclination angle based on an electrical capacitance of the capacitor that is dependent on the inclination angle of the liquid. A capacitive inclination sensor is known, for example, from German Patent Disclosure DE 41 41 324 A1.

A micromechanical inclination sensor for ascertaining the respective inclination based on the inclination-dictated position of a seismic mass permits the inclination to be ascertained. One such inclination sensor with a seismic mass in the form of a rotor whose position can be ascertained capacitively is known, for example, from German Patent Disclosure DE 41 06 932 A1. This may be considered as a form of accelerometer, of which various configurations may also be used.

Other inclination sensors suitable for ascertaining the inclination angle of the water phantom are also known, for example from motor vehicle anti-theft systems, air bag deployment systems and the like. Besides the aforementioned inclination sensors, thermodynamic inclination sensors can also be used for ascertaining the inclination, for example, those developed by the Institut für Mikro-und Informationstechnik der Hahn-Schickard-Gesellschaft e.V. [Institute for Microtechnology and Information Technology of the Hahn-Schickard Association] (HSG-IMIT) (Stuttgart, Germany) and Vogt electronic AG (Obernzell 94130, Germany).

In addition to the two inclination sensors 42, the water phantom 1 may have a spacing sensor 43, in a predetermined spatial arrangement with respect to the positioning device 4. The spacing sensor 43 ascertains the orientation of the positioning device 4 with respect to the water surface 23 based on a spacing f from a proximal point 44 of the water surface 23. The spacing sensor 43 is disposed on the rod 22 of the positioning device, near the detector 5. The spacing f between the spacing sensor 43 and the water surface 23 can be ascertained, for example, with the aid of a laser beam, emitted by the spacing sensor 43 in the direction of a proximal point 44 on the water surface 23 and reflected from there back to the spacing sensor 43. Based on this spacing f, the immersion depth e can be ascertained taking into account the distance between the optical spacing sensor 43 and the detector 5. The spacing g of the third retaining device 21 from the water surface 23 can be ascertained, taking into account the position of the rod 22 relative to the third retaining device 21. The knowledge of the vertical position, especially in the case of a vertical ionizing radiation direction from above the water phantom 1, is relevant for evaluating the particular radiation measurement outcomes. By disposing the spacing sensor 43 directly on the positioning device 4, the vertical position, and the immersion depth e, relative to the water surface 23 can be ascertained accurately. Moreover, the knowledge of the spacing f of the spacing sensor 43 from the water surface 23 also makes it possible to monitor the water level h.

The water phantom 1 may be equipped with a display 45 for displaying the orientation thereof. As such, the orientation is easily recognizable by a user of the water phantom 1. The user can correct the orientation or can evaluate the outcomes of the measurements, accounting for the orientation. The orientation, which may be in the form of an inclination, may be forwarded by the inclination sensor 42 via a data connection cable 46 to the display 45 and displayed thereon an liquid crystal (LC) display 47 or other similar display device. Furthermore, the display 45 may be configured to display the vertical position of the positioning device 4 relative to the water surface 23. Other connections between the sensors and the display are not shown in the drawing. Further, the display 45 may be positioned separately from the water phantom 1.

At least one orientation device 48 and 49 orient the positioning device 4 relative to the water surface 23 to an intended orientation as a function of the ascertained orientation. The orientation is adjustable to an intended orientation, such as before the measurement of the radiation.

In a further embodiment, the positioning device 4 may be oriented in the container 3, such that the positioning device 4 is disposed in a predetermined relative position. The fastening elements 12-15 may orient the positioning device 4. As a result, the sidewalls of the container 3 can also be aligned with the positioning device 20. For instance, in orienting the third rail 20 parallel to the water surface 23, the outer walls of the container 3 can be vertically oriented simultaneously, so that radiation striking one of the sidewalls horizontally strikes the applicable sidewall at a right angle which may simplify the interpretation of the measurements.

In another example, four adjustable-height feet are disposed below the container 3 near the corners thereof. Two of the feet, 48 and 49, are shown in FIG. 2. These orientation devices 48, 49 permit manual orientation of the positioning device 4, such as with the aid of the display 45. The feet 48 and 49 may each include a respective frame 50 and 51, secured to the underside of the container 3. Each frame 51, 52 has a circular opening with a threaded hole on the underside thereof. Screws 52 and 53 are engaged with these threaded holes. A stand support 54 and 55 is disposed on a lower end of each screw 52, 53 to distribute the weight of the water phantom 1. By screwing the screws 52 and 53 inward and outward as needed, the extension length 57 and 58 of the respective screws 52 and 53 out of the frame 48 and 49, and thus the orientation of the container 3 and the positioning device 4, are adjustable. Moreover, by jointly screwing the screws 52, 53 in and out, the vertical position of the positioning device 4 relative to the water surface 23 is also adjustable.

Figure 3:
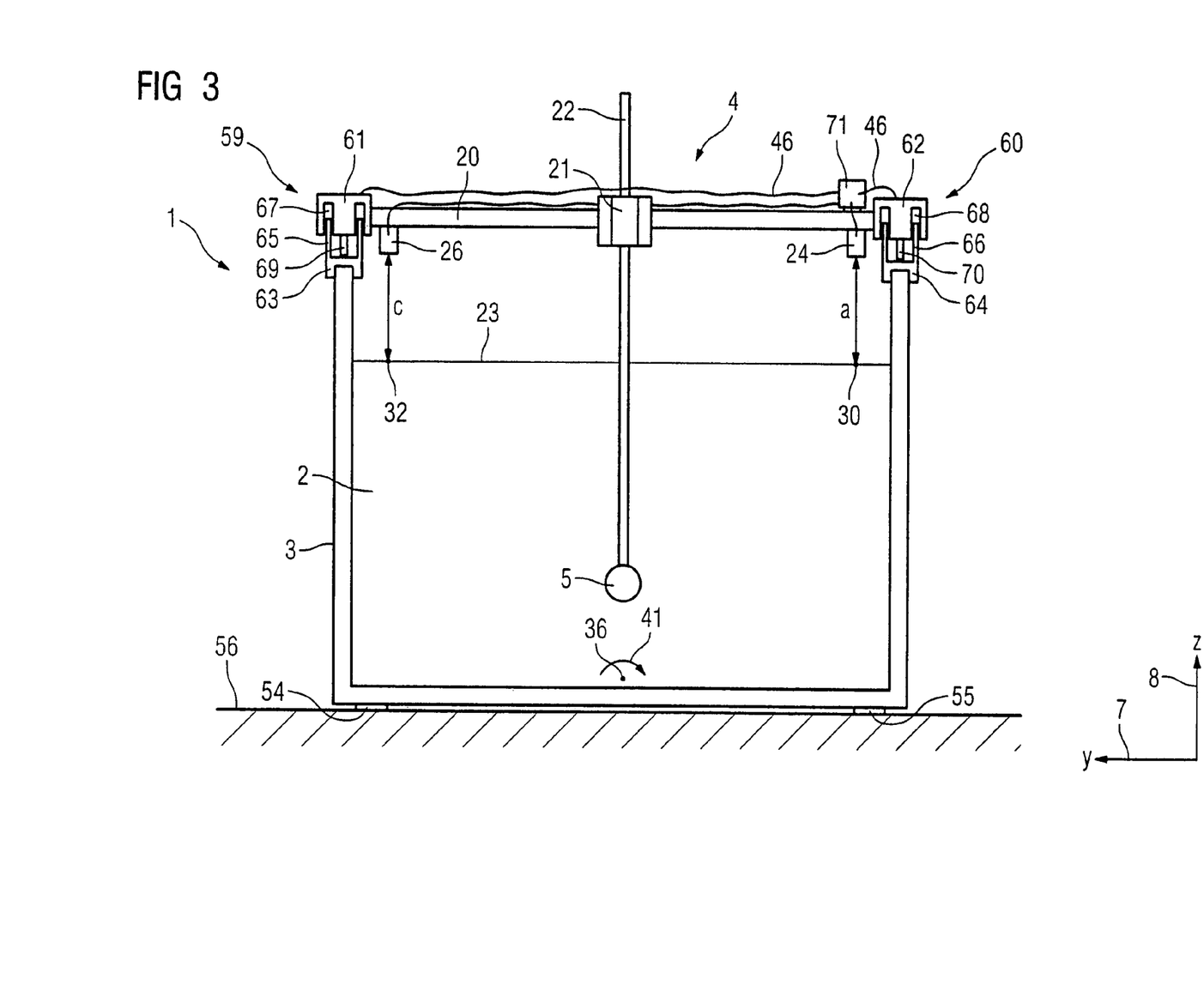
FIG. 3 shows a side view of a water phantom as in FIG. 2, in which the orientation of the positioning device is ascertainable with the aid of spacing sensors located in the positioning device and is adjustable relative to the container by means of adjustable-height fastening elements.

FIG. 3 shows another side view of the water phantom 1 of FIG. 1. Acoustic spacing sensors 26 and 24 are disposed on the positioning device 4. The orientation of the positioning device 4 can be ascertained directly. In this example, the two spacing sensors 26 and 24 are disposed close to the ends of the third rail 20 so that, based on the distances c and a measured by the respective spacing sensors 26 and 24 from the respective proximal points 32 and 30 on the water surface 23, the orientation can be ascertained, for example, in the form of an inclination about the axis of inclination 36 that is parallel to the x axis 6. Similarly, further spacing sensors may be disposed on the positioning device 4, for example on the second rail 17, so that the inclination about the axis of inclination 38 that is parallel to the y axis 7 can also be ascertained.

The container 3, in this example, rests on stand supports 54, 55 located at the corners of the container 3 on the surface 56 which may not be adjustable in height. Alternatively, the supports 54, 55 are adjustable in height.

The orientation may be provided by four lifting elements, which are disposed on the upper corners of the container 3 in place of fastening elements 12-14. Of the four lifting elements, in this side view only the front two lifting elements 59 and 60 are shown, each in cross section. The lifting elements 59 and 60 each include a respective lower part 61 and 62, which is secured to a respective corner of the container 3, and a respective upper part 63 and 64, to which either the first rail 16 or the second rail 17 of the positioning device 4 is secured. The lower part 61 and 62 of each lifting element 59 and 60, respectively, reaches, each with two vertically upward-oriented guide bolts 65 and 66, into corresponding bores 67 and 68 in the upper part 61 and 62. Because of this form-locking engagement with one another, both parts 61, 63 and 62, 64 are guided vertically and are each adjustable in lifting height. Each of the lifting elements 59, 60 may have a drive for automatically orienting the positioning device 4. The lifting elements 59 and 60 are adjustable in their respective lifting height by lifting bolts 69 and 70 that can be extended by a drive from the respective upper part 61 and 61 in the direction of the respective lower part 63 and 64. The drive may for instance include an electric motor, hydraulics or pneumatics.

The orientation of the positioning device 4 may be automatically adjusted to an intended orientation with the aid of the lifting elements 59, 60 prior to making the radiation measurements. A control unit 71 may be located on the positioning device 4 which receives the various spacing distances determined by the spacing sensors 24, 26 via data connection cables 46 and sends control signals to the lifting elements 59, 60 via further data connection cables 46.

Figure 4:
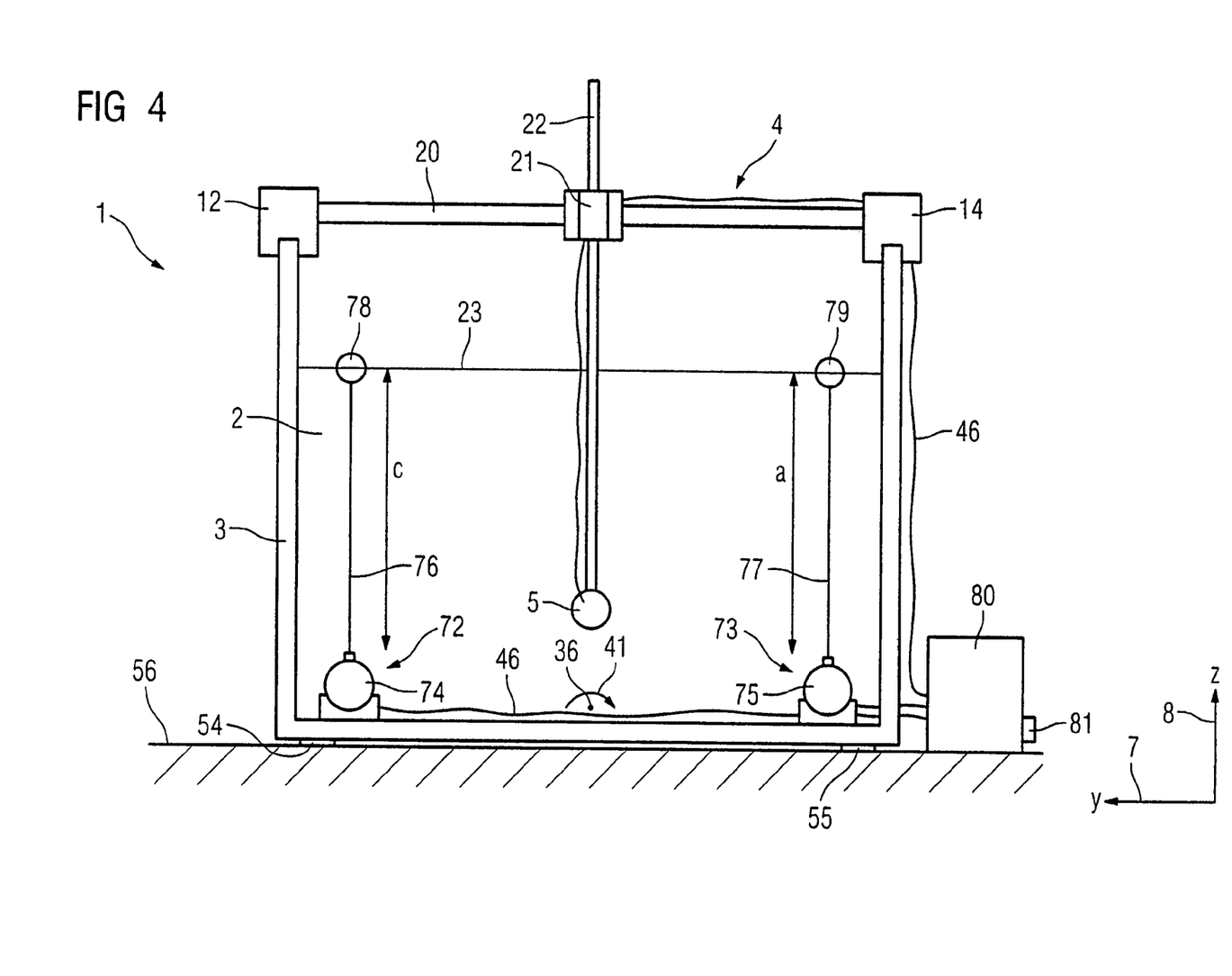
FIG. 4 shows a side view of a water phantom as in FIG. 3, in which the orientation of the positioning device is ascertainable with the aid of mechanical spacing sensors located in the container.

FIG. 4 shows a side view of a water phantom 1 as in FIG. 3, with mechanical spacing sensors 72, 73 located on the bottom of the container. The mechanical spacing sensors 72 and 73 each include a Bowden cable potentiometer 74 and 75, respectively, whose Bowden cable 76 and 77 can be pulled out as far as the water surface 23 by a respective float 78 and 79 secured to the end of the respective Bowden cable 76 and 77. The determined distances c and a may be forwarded via data connection cables 46 to an evaluation unit 80 which may be located outside the container 3, and may be separated there from. The various values measured by the detector 5 and forwarded to the evaluation unit 80 via a data connection cable 46 can be evaluated, taking into account the particular orientation of the positioning device 4 ascertained based on the measured distances. The evaluated measurement data can be forwarded via an interface 81 to a computer, a data memory, a data output unit, or to a data network. To avoid lateral drifting of the float 78, the float can additionally be guided by a vertically oriented tube (not shown) which, for each arbitrary spacing c, rests with its inner wall on the float without preventing the float from moving vertically.

Although only a few exemplary embodiments of this invention have been described in detail above, those skilled in the art will readily appreciate that many modifications are possible in the exemplary embodiments without materially departing from the novel teachings and advantages of the invention. Accordingly, all such modifications are intended to be included within the scope of this invention as set forth in the following claims.

The invention claimed is:

1. A water phantom for measuring ionizing radiation, the phantom comprising:
   a container for a fluid;
   a radiation detector;
   a positioning device for positioning the radiation detector with respect to the container; and
   a first spacing sensor for ascertaining orientation of the positioning device relative to a surface of the fluid, the first spacing sensor disposed in the fluid.

2. The phantom of claim 1,
   wherein the first spacing sensor measures a distance between the first spacing sensor and a first proximate point of the surface of the fluid.

3. The phantom of claim 2, further comprising at least two additional spacing sensors, the spacing sensor and the at least two additional spacing sensors defining a triangle.

4. The phantom of claim 3, where the triangle is a right triangle.

5. The phantom of claim 2, further comprising a device for orienting the positioning device with respect to the surface.

6. The phantom of claim 5, further comprising a control unit configured to automatically position the detector by orientation of the positioning device.

7. The phantom of claim 6, wherein the control unit is configured to use a vertical distance of the positioning device relative to the water surface in the automatic positioning of the detector by orientation of the positioning device.

8. The phantom of claim 6, further comprising an evaluation unit for determining the measured radiation parameters as a function of the orientation of the positioning device.

9. The phantom of claim 8, wherein the evaluation unit determines the measured radiation parameters as a function of the vertical distance of the positioning device with respect to the surface.

10. The phantom of claim 2, wherein the spacing sensor is based on a transit time of ultrasound waves reflected at the surface.

11. The phantom of claim 2, wherein the spacing sensor is based on light reflected at the fluid surface.

12. The phantom of claim 2, wherein the spacing sensor and at least another spacing sensor are disposed on the positioning device.

13. The phantom of claim 2, wherein position of the positioning device with respect to the surface is determined from the distance measured by the spacing sensor.

14. The phantom of claim 1, wherein the spacing sensor and at least another spacing sensor are disposed in the container in a predetermined relative position with respect to the positioning device.

15. The phantom as claimed in claim 1, further comprising a second spacing sensor that measures a distance between the second spacing sensor and a second proximate point of the surface of the fluid, wherein the first and second spacing sensors are used for ascertaining an inclination of the positioning device about an axis of inclination perpendicular to a line between the first and second spacing sensors.

16. A water phantom for measuring an ionizing radiation, the phantom comprising
a container for fluid;
a radiation detector;
a positioning device for positioning the detector in various measurement positions within container;
an inclination sensor disposed in a predetermined spatial arrangement with respect to the positioning device.

17. The phantom of claim 16, wherein the inclination sensor is operable to measure an inclination angle with respect to a local gravity vector.

18. The phantom of claim 17, having the inclination sensor and another inclination sensor disposed at an angle to one another, for ascertaining the inclination about two respective axes of inclination.

19. The phantom of claim 18, wherein the two axes of inclination are orthogonally disposed.

20. The phantom of claim 16, wherein the inclination sensor comprises electrodes immersable at least partially into an electrically conductive liquid, the inclination sensor operable to determine an inclination angle based on an electrical resistance value between the electrodes.

21. The phantom of claim 16, wherein the inclination sensor comprises a capacitor fillable at least partly with an electrically conductive or dielectric liquid, the inclination sensor operable to determine an inclination angle based on an electrical capacitance value.

22. The phantom of claim 16, wherein the inclination sensor is operable to determine an inclination angle based on an inclination-related position of a seismic mass.

23. The phantom of claim 22, wherein the position of the seismic mass is capacitively determined.

24. The phantom of claim 16, further comprising a spacing sensor disposed with respect to the positioning device for ascertaining a vertical position of the positioning device relative to a surface of the fluid based on a distance of the spacing sensor from the surface.

25. The phantom of claim 16 further comprising a display operable to display an inclination angle.

26. A water phantom for measuring an ionizing radiation, comprising:
a container for water;
a radiation detector; and
means for determining a position of the radiation detector with respect to a water surface, the means for determining being disposed in the water.

27. The device of claim 26, further comprising means for positioning the radiation detector.

28. The device of claim 27, further comprising means for displaying an orientation of the means for positioning.

29. The device of claim 28, wherein the means for displaying displays a vertical position of the means for positioning with respect to the water surface.

30. The device of claim 28, wherein a means for orientation orients the means for positioning by orienting the container on which the means for positioning is disposed in a predetermined relative position with respect to the container.

31. The device of claim 27, wherein a means for orientation automatically orients the means for positioning.

32. The device of claim 31, wherein the means for orientation orients the means for positioning with respect to the container.

* * * * *